(12) United States Patent
Purcell

(10) Patent No.: US 7,594,724 B2
(45) Date of Patent: Sep. 29, 2009

(54) DEVICE FOR USE WITH AN EYE PROTECTOR

(75) Inventor: Ricky Wayne Purcell, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 165 days.

(21) Appl. No.: 12/006,026

(22) Filed: Dec. 28, 2007

(65) Prior Publication Data
US 2009/0165189 A1   Jul. 2, 2009

(51) Int. Cl.
*G02C 3/00*   (2006.01)
(52) U.S. Cl. .................. 351/156; 351/157; 351/158
(58) Field of Classification Search ............... 351/156, 351/157, 158
See application file for complete search history.

(56) References Cited

U.S. PATENT DOCUMENTS

| | | | |
|---|---|---|---|
| 3,397,026 A | 8/1968 | Spina | |
| 4,998,816 A | 3/1991 | Eggenberger et al. | |
| 5,475,449 A | 12/1995 | Pyle | |
| 5,541,677 A | 7/1996 | Huhtala | |
| 5,655,263 A | 8/1997 | Stoller | |
| 5,664,291 A | 9/1997 | Stoller | |
| 5,806,526 A | 9/1998 | Rhoad | |
| 6,074,060 A | 6/2000 | Bruce | |
| 6,340,227 B1 | 1/2002 | Solberg et al. | |
| 6,533,413 B2 | 3/2003 | Wright et al. | |
| 6,604,823 B2 * | 8/2003 | Hursey, Jr. .................. | 351/61 |
| 6,941,619 B2 | 9/2005 | Mackay et al. | |
| 7,213,916 B1 | 5/2007 | Pettett | |

FOREIGN PATENT DOCUMENTS

| | | |
|---|---|---|
| EP | 0 870 487 B1 | 6/2004 |
| WO | WO 02/073292 A2 | 9/2002 |

* cited by examiner

*Primary Examiner*—Huy K Mai
(74) *Attorney, Agent, or Firm*—Michael J. Bendel

(57) ABSTRACT

A device and method for locating a pair of ear engaging members and an eye protector in proximity to a user's head. This includes a cord with a length and a dual mode adjustment member located along the length of the cord. An ear end of the cord can have a pair of ear engaging members joined thereto. An eye end of the cord has a pair of eye protector connectors joined thereto. The dual mode adjustment member is positionable along the length of the cord to a first mode and to a second mode shortens that, respectively, lengths or shortens the cord between the adjustment member and the eye end of the cord.

20 Claims, 2 Drawing Sheets

DEVICE FOR USE WITH AN EYE PROTECTOR

BACKGROUND OF THE INVENTION

The present invention relates generally to devices for locating equipment about a user, and more particularly to such devices being used to enhance the features of personal safety devices worn by a user about their head, such as eye protectors and ear engaging members (e.g., hearing protectors).

The need for locating equipment about a user, and in particular their head has long been recognized among those concerned with convenience as well as health and safety issues. However, most experts in this field would acknowledge that this effort has room for needed improvements. For example, personal protective devices have proliferated, yet there still remain needs to enhance convenience and/or use compliance. Workers who should use these devices often do not, or use them only under duress from their employers. The lack of worker compliance with safety rules is exacerbated by the fact that currently available personal protection enhancement devices are often uncomfortable, clumsy to use, to limited in their use, and/or perform poorly. Fortunately, as personal equipment and personal protection devices become more comfortable and perform better, worker compliance with their use should also improve.

Accordingly, while various types of personal equipment locating devices exist in the art, there remains a need for a device that helps overcome one or more of the aforementioned problems. The applicant has surprisingly invented such a device, as discussed further herein.

SUMMARY OF THE INVENTION

Various definitions used throughout the specification and claims are provided first, followed by a description of various aspects of the invention.

As used herein, "join" or "joined" or "joining" mean the connecting, adhering, bonding, attaching, or the like, of two elements, either permanently or temporarily (e.g., a fitted relationship, a snap together-apart relationship, and the like). Two elements will be considered to be joined together when they are joined directly to one another or indirectly to one another, such as when each is directly connected to intermediate elements.

As used herein, "ear engaging member(s)" means any device intended to be located in proximity of a user's ear, for example, for noise protection (e.g., earplugs, ear muffs, and the like) or sound location (e.g., hearing aid, channeling sound to the ear canal such as music or telephone conversation, and the like).

As used herein, "eye protector" means any device intended to be located in proximity of a user's eyes or face, for example, for shielding the eyes from foreign objects approaching the face (e.g., safety glasses, goggles, and the like).

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

In one aspect of the present invention, there is provided a device for locating a pair of ear engaging members and an eye protector in proximity to a user's head. The device includes a cord including (i) a length with an ear end and an opposite eye end and (ii) a dual mode adjustment member located along the length of the cord between the ear and eye ends. The ear end of the cord includes a left ear end and a right ear end, where each left and right ear end can have one of the pair of ear engaging members joined thereto. The eye end of the cord includes a left eye end and a right eye end, where each left and right eye end has an eye protector connector joined thereto. The dual mode adjustment member is positionable along the length of the cord: (i) to a first mode that adjustably shortens the length of the cord between the adjustment member and the eye end of the cord to thereby provide a force to tension the eye protector connectors toward each other, and (ii) to a second mode that adjustably lengthens the length of the cord between the adjustment member and the eye end of the cord to thereby reduce the force of tension between the eye protector connectors and enable them to be moved further away from each.

In another aspect of the present invention, there is provided a device for use with an eye protector in proximity to a user's head. The device includes a cord including (i) a length with an ear end and an opposite eye end and (ii) a dual mode adjustment member located along the length of the cord between the ear and eye ends. The ear end of the cord includes a left ear end and a right ear end, where each left and right ear end has an ear engaging member joined thereto. The eye end of the cord includes a left eye end and a right eye end, where each left and right eye end has an eye protector connector joined thereto. The dual mode adjustment member is positionable along the length of the cord: (i) to a first mode that adjustably shortens the length of the cord between the adjustment member and the eye end of the cord to thereby provide a force to tension the eye protector connectors toward each other, (ii) to a second mode that adjustably lengthens the length of the cord between the adjustment member and the eye end of the cord to thereby reduce the force of tension between the eye protector connectors and enable them to be moved further away from each, and (iii) in both the first and second modes the left and right ear ends of the cord are isolated from the eye protector connectors such that (a) the left and right ear ends of the cord can hang from the user while not in use without disturbing operation of the eye protector connectors in use and (b) the eye protector connectors can hang from the user while not in use without disturbing operation of the left and right ear ends of the cord in use.

In still another aspect of the present invention, there is provided a method for connecting together a pair of ear engaging members and a pair of eye protector connectors. The method includes providing a cord including (i) a length with an ear end and an opposite eye end and (ii) a dual mode adjustment member located along the length of the cord between the ear and eye ends. The ear end of the cord including a left ear end and a right ear end and the eye end of the cord including a left eye end and a right eye end. There is also joining an ear engaging member to each left and right ear end. And, joining an eye protector connector to each left and right eye end. And also, positioning the dual mode adjustment member along the length of the cord to (i) a first mode that adjustably shortens the length of the cord between the adjustment member and the eye end of the cord to thereby provide a force to tension the eye protector connectors toward each other, and (ii) a second mode that adjustably lengthens the length of the cord between the adjustment member and the eye end of the cord to thereby reduce the tension between the eye protector connectors and enable them to be moved further away from each other.

In yet another aspect of the present invention there is provided a method for locating a pair of ear engaging members with an eye protector in proximity to a user's head. This includes providing a cord including (i) a length with an ear end and an opposite eye end and (ii) a dual mode adjustment member located along the length of the cord between the ear and eye ends. The ear end of the cord including a left ear end and a right ear end and the eye end of the cord including a left eye end and a right eye end. This further includes joining an ear engaging member to each left and right ear end. And, joining an eye protector connector to each left and right eye end. And further, joining the eye protector connectors to the eye protector. And also, positioning the dual mode adjustment member along the length of the cord to (i) a first mode that adjustably shortens the length of the cord between the adjustment member and the eye end of the cord to thereby provide a force to tension the eye protector connectors toward each other and thereby secure the eye protector to the user's head, and (ii) a second mode that adjustably lengthens the length of the cord between the adjustment member and the eye end of the cord to thereby reduce the tension between the eye protector connectors and enable them to be moved further away from each and thereby unsecure the eye protector from the user's head.

Other features of the invention relate to particular configurations of the cord, the dual mode adjustment member, and a break-away connection.

Still other features of the invention will be in part apparent and in part pointed out hereinafter as well as better understood by practice of the invention.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the device and method that is the present invention.

BRIEF DESCRIPTION OF THE DRAWINGS

Corresponding reference characters indicate corresponding parts throughout the drawings.

DETAILED DESCRIPTION

Figure 1:
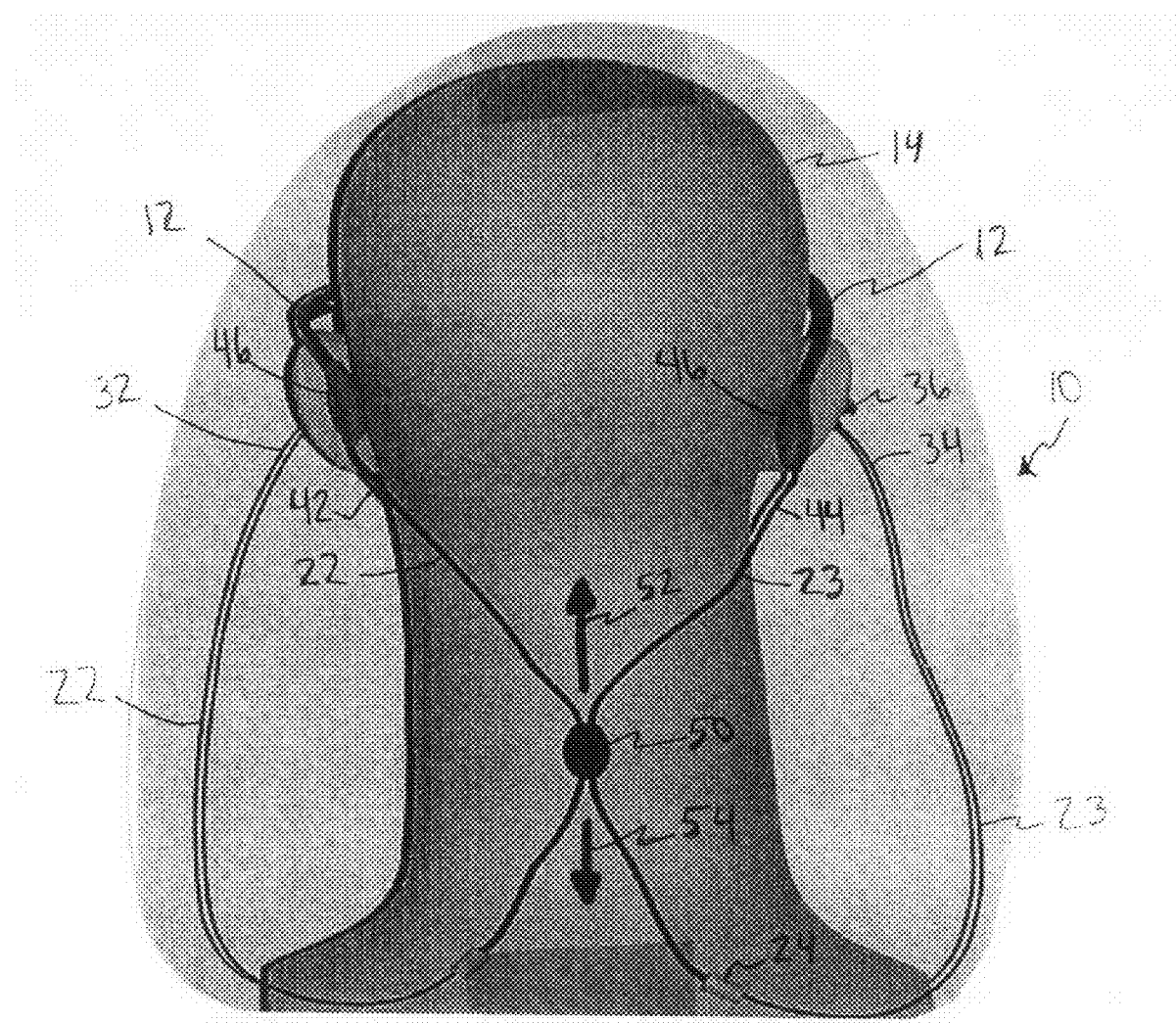
FIG. 1 is a perspective view of the invention, connected to an eye protector and on a user's head.
Figure 2:
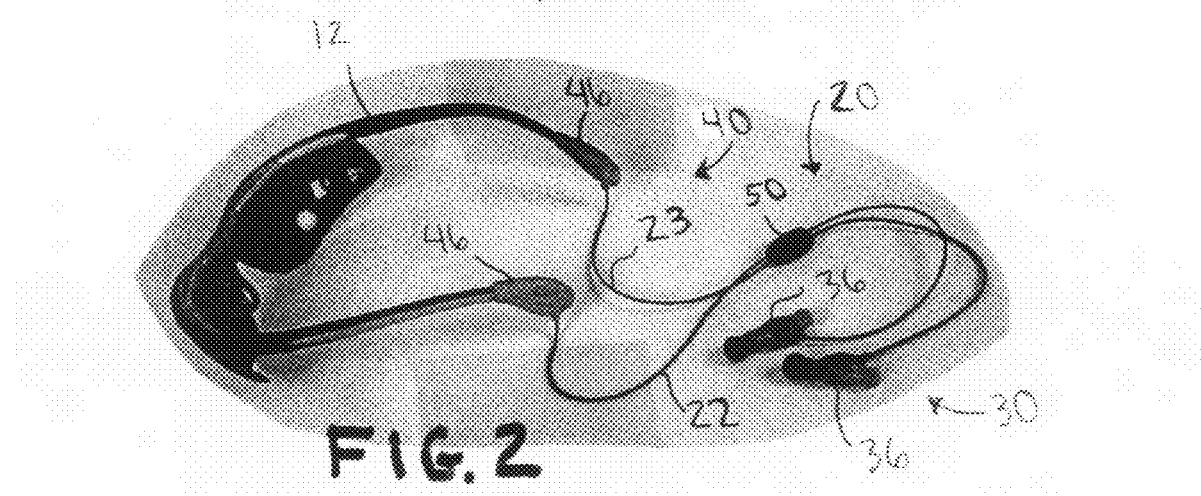
FIG. 2 is a perspective view of an alternative embodiment of the invention, connected to an eye protector and not on a user.
Figure 3:
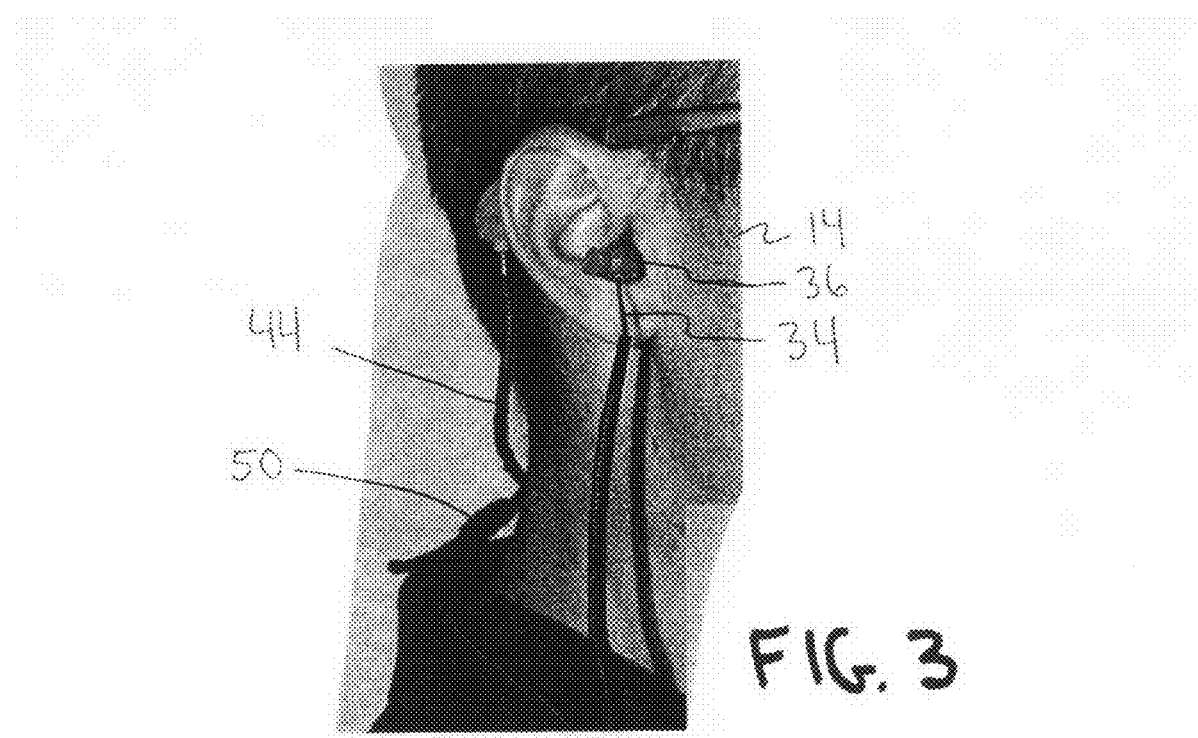
FIG. 3 is a perspective view of a user's head right side, with the invention connected to an eye protector on the user's head.
Figure 4:
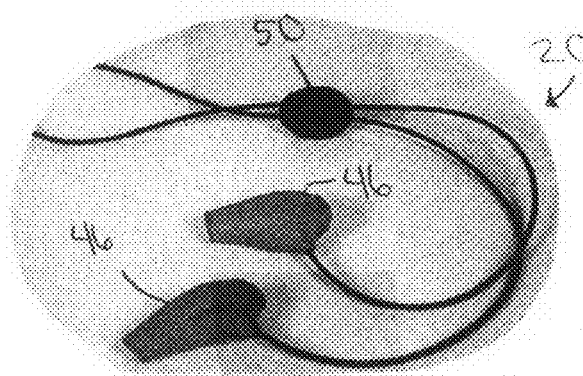
FIG. 4 is a perspective view of a portion of the invention.

Referring now to the drawings and in particular FIGS. 1-4 for example, there is depicted a device 10 for locating a pair of ear engaging members 36 and an eye protector 12 in proximity to a user's head 14. Device 10 includes a cord 20. The cord has a length with an ear end 30 and an opposite eye end 40, and a dual mode adjustment member 50 located along the length of the cord between the ear and eye ends. Ear end 30 of the cord has a left ear end 32 and a right ear end 34, and each left and right ear end can have one of the pair of ear engaging members 36 joined thereto. Eye end 40 of the cord has a left eye end 42 and a right eye end 44, and each left and right eye end has an eye protector connector 46 joined thereto.

Dual mode adjustment member 50 is positionable along the length of cord 20 in two modes. There is a first mode 52 that adjustably shortens the length of the cord between adjustment member 50 and eye end 40 of the cord to thereby provide a force to tension eye protector connectors 46 toward each other, for example, when the user wants to secure the eye protectors about his/her head. And, there is a second mode 54 that adjustably lengthens the length of cord 20 between adjustment member 50 and eye end 40 of the cord to thereby reduce the force of tension between eye protector connectors 46 and enable them to be moved further away from each other, for example, when the user wants to remove the eye protectors from his/her head.

Without being limited to a particular theory of understanding, and while not required, it may be further advantageous in the first mode 52 that the left and right ear ends 32, 34 of the cord are isolated from the eye protector connectors 46 such that the left and right ear ends of the cord can hang from the user while not in use without disturbing operation of the eye protector connectors in use. For example, this can be useful when the user removes one or both ear engaging members from proximity of their ears but still desires to keep the eye protector secured to their head. Additionally or alternatively, it may be further advantageous in the second mode 54 that the left and right ear ends 32, 34 of the cord are isolated from the eye protector connectors 46 such that the eye protector connectors can hang from the user while not in use without disturbing operation of the left and right ear ends of the cord in use. For example, this can be useful when the user removes the eye protector connectors from the eye protector or removes the eye protector (with the eye protector connectors still attached) from proximity of their head but still desires to keep one or both ear engaging members in proximity to their ears, e.g., in their ears. In one or both of these ways, the device physically isolates the operation of the ear engaging members from the eye protector connectors so each can function independent of the other and provide the user with great convenience for enhanced device use flexibility.

In other aspects of the invention there is provided the cord being made of two distinct strands 22, 23, with one set of ends of the strand being the ear end 30 and a second set of ends being the opposite eye end 40. The strands 22, 23 may be positioned near each other, for example, via the dual mode adjustment member. Still further, it may be that the dual mode adjustment member surrounds a portion of the length of cord 20, e.g., the strands pass through adjustment member 50, between ear and eye ends 30, 40. Adjustment member 50 may frictionally engage cord 20 and/or strands 22, 23 to adjustably shorten or lengthen the length of cord/strands between adjustment member 50 and the eye end 40.

Figure 5:
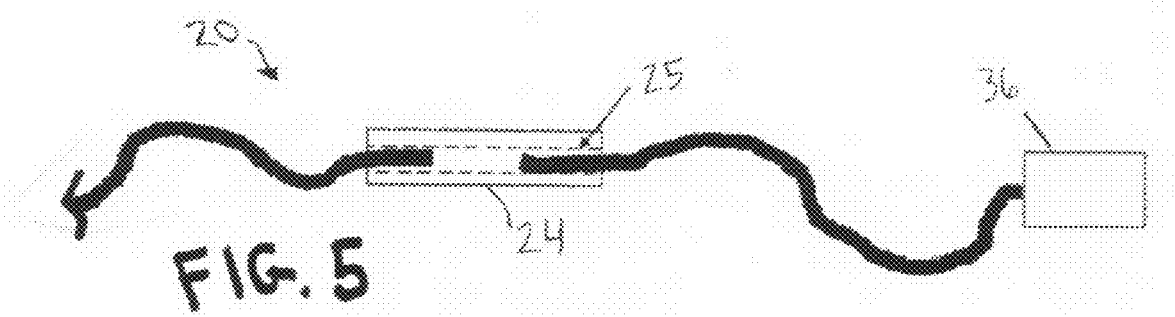
FIG. 5 is an enlarged diagrammatic view of a portion of the invention that features a break-away connection.

In yet another aspect of the invention, at least one of left ear end 32, right ear end 34, left eye end 42, and the right eye end 44, may be a break-away connection 24. If used, such break-away connection 24 would join respective ear engaging member 36 to ear ends 32 and/or 34 and/or eye protector connector 46 to eye ends 42 and/or 44. Connection 24 can be employed by any size fit relationship between two parts or similarly resulting mechanical relationship. FIG. 5 shows one example where cord or strand 20, 22, 23 snuggly fits inside break-away connection channel 25 such that friction maintains the two parts together but if a force in excess of the static friction force holding the parts together is experienced, then the two parts separate at connection 24. While FIG. 5 expressly shows cord or strand on both sides of connection 24, ear engaging member 36 depicted can have the same type of break-away connection where the strand or cord is inserted into the member 36 (and similarly possible with eye protector connectors 46) in a fitted relationship. Without being limited to a theory of understanding or advantage, these features can enhance the versatility of device 20 by enabling easy substitution of parts of the device or of other parts with the device, for example, ear engaging members and in particular earplugs. Also, for example, connector 24 may be oval in shape. This can allow for easy replacement as pressing the oval in the long ways direction "opens" it for easy insertion of a new component, but other shapes can work also.

The device parts may be made of a homogeneous material or a composite material, and may include one or more layers. Eye protector connectors 46 may be made from a flexible material that is injection or blow moldable into a bulb that does not permanently deform when stressed by stretching (e.g., when putting onto and removing from eye protector 12. Examples could be polyurethane, santoprene, polyethylene, or polypropylene. Adjustment member 50 may be made from flexible and/or elastic materials such as polyurethane, santoprene, polyethylene, or polypropylene, that may be formed or molded. For cord 20 and strands 22, 23, these may be shoe strand like materials or other molded, extruded or formed materials as are common for lanyard devices.

In other aspects of the invention there is provided a method for connecting together the pair of ear engaging members 36 and the pair of eye protector connectors 46. The method includes providing cord 20 having a length with ear end 30 and opposite eye end 40 and dual mode adjustment member 50 located along the length of the cord between the ear and eye ends. The ear end of the cord includes left ear end 32 and right ear end 34. The eye end of the cord comprises left eye end 42 and right eye end 44. The method further includes joining ear engaging member 36 to each left and right ear end 32, 34. Also, there is joining eye protector connector 46 to each left and right eye end 42, 44. Finally, the method includes positioning the dual mode adjustment member along the length of the cord to (i) first mode 52 that adjustably shortens the length of the cord between the adjustment member 50 and the eye end 40 of the cord to thereby provide the force to tension the eye protector connectors 46 toward each other, and (ii) second mode 54 that adjustably lengthens the length of the cord between the adjustment member 50 and the eye end 40 of the cord to thereby reduce the tension between the eye protector connectors 46 and enable them to be moved further away from each. This method can further include optional steps consistent with the structures of the invention as previously described. Finally, and while not limiting, it can be advantageous to practice the steps of the invention sequentially in the order discussed in this paragraph.

In still other aspects, there is provided a method for locating the pair of ear engaging members 36 with eye protector 12 in proximity to user's head 14. This includes providing cord having a length with ear end 30 and opposite eye end 40 and dual mode adjustment member 50 located along the length of the cord between the ear and eye ends. The ear end of the cord includes left ear end 32 and right ear end 34. The eye end of the cord includes left eye end 42 and a right eye end 44. There is also joining ear engaging member 36 to each left and right ear end 32, 34. Further also, joining eye protector connectors 46 to each left and right eye end 42, 44. And, there is joining the eye protector connectors to the eye protector 12. The method further includes positioning the dual mode adjustment member 50 along the length of the cord 20 to first mode 52 that adjustably shortens the length of the cord between the adjustment member 50 and the eye end 40 of the cord to thereby provide a force to tension the eye protector connectors 46 toward each other and thereby secure the eye protector to the user's head. Finally, the method includes positioning the dual mode adjustment member 50 along the length of the cord 20 to second mode 54 that adjustably lengthens the length of the cord between the adjustment member 50 and the eye end 40 of the cord to thereby reduce the tension between the eye protector connectors 46 and enable them to be moved further away from each other and thereby unsecure the eye protector 12 from the user's head. This method can further include optional steps consistent with the structures of the invention as previously described. Finally, and while not limiting, it can be advantageous to practice the steps of the invention sequentially in the order discussed in this paragraph.

As various changes could be made in the above constructions and methods, without departing from the scope of the invention, it is intended that all matter contained in the above description and shown in the accompanying drawings shall be interpreted as illustrative and not in a limiting sense.

What is claimed is:

1. A device for locating a pair of ear engaging members and an eye protector in proximity to a user's head, comprising:
    a cord comprising (i) a length with an ear end and an opposite eye end and (ii) a dual mode adjustment member located along the length of the cord between the ear and eye ends;
    the ear end of the cord comprising a left ear end and a right ear end wherein each left and right ear end can have one of the pair of ear engaging members joined thereto;
    the eye end of the cord comprising a left eye end and a right eye end wherein each left and right eye end has an eye protector connector joined thereto; and,
    the dual mode adjustment member is positionable along the length of the cord:
        (i) to a first mode that adjustably shortens the length of the cord between the adjustment member and the eye end of the cord to thereby provide a force to tension the eye protector connectors toward each other, and
        (ii) to a second mode that adjustably lengthens the length of the cord between the adjustment member and the eye end of the cord to thereby reduce the force of tension between the eye protector connectors and enable them to be moved further away from each.

2. The device of claim 1 wherein the cord comprises two distinct strands with one set of ends being the ear end and a second set of ends being the opposite eye end.

3. The device of claim 1 wherein the cord comprises two distinct strands that are positioned near each other by the dual mode adjustment member.

4. The device of claim 1 wherein the dual mode adjustment member surrounds a portion of the length of the cord between the ear and eye ends and frictionally engages the cord to adjustably shorten or lengthen the length of the cord between the adjustment member and the eye end of the cord.

5. The device of claim 1 wherein at least one of the left ear end, the right ear end, the left eye end, and the right eye end comprises a break-away connection that joins its respective ear engaging member or eye protector connector thereto.

6. A device for use with an eye protector in proximity to a user's head, comprising:
    a cord comprising (i) a length with an ear end and an opposite eye end and (ii) a dual mode adjustment member located along the length of the cord between the ear and eye ends;
    the ear end of the cord comprising a left ear end and a right ear end wherein each left and right ear end has an ear engaging member joined thereto;
    the eye end of the cord comprising a left eye end and a right eye end wherein each left and right eye end has an eye protector connector joined thereto; and, the dual mode adjustment member is positionable along the length of the cord:
- (i) to a first mode that adjustably shortens the length of the cord between the adjustment member and the eye end of the cord to thereby provide a force to tension the eye protector connectors toward each other,
- (ii) to a second mode that adjustably lengthens the length of the cord between the adjustment member and the eye end of the cord to thereby reduce the force of tension between the eye protector connectors and enable them to be moved further away from each, and
- (iii) in both the first and second modes the left and right ear ends of the cord are isolated from the eye protector connectors such that (a) the left and right ear ends of the cord can hang from the user while not in use without disturbing operation of the eye protector connectors in use and (b) the eye protector connectors can hang from the user while not in use without disturbing operation of the left and right ear ends of the cord in use.

7. The device of claim 6 wherein the cord comprises two distinct strands with one set of ends being the ear end and a second set of ends being the opposite eye end.

8. The device of claim 6 wherein the cord comprises two distinct strands that are positioned near each other by the dual mode adjustment member.

9. The device of claim 6 wherein the dual mode adjustment member surrounds a portion of the length of the cord between the ear and eye ends and frictionally engages the cord to adjustably shorten or lengthen the length of the cord between the adjustment member and the eye end of the cord.

10. The device of claim 6 wherein at least one of the left ear end, the right ear end, the left eye end, and the right eye end comprises a break-away connection that joins its respective ear engaging member or eye protector connector thereto.

11. A method for connecting together a pair of ear engaging members and a pair of eye protector connectors, comprising:
providing a cord comprising (i) a length with an ear end and an opposite eye end and (ii) a dual mode adjustment member located along the length of the cord between the ear and eye ends, wherein the ear end of the cord comprises a left ear end and a right ear end and the eye end of the cord comprises a left eye end and a right eye end;
joining an ear engaging member to each left and right ear end;
joining an eye protector connector to each left and right eye end; and,
positioning the dual mode adjustment member along the length of the cord to (i) a first mode that adjustably shortens the length of the cord between the adjustment member and the eye end of the cord to thereby provide a force to tension the eye protector connectors toward each other, and (ii) a second mode that adjustably lengthens the length of the cord between the adjustment member and the eye end of the cord to thereby reduce the tension between the eye protector connectors and enable them to be moved further away from each other.

12. The method of claim 11 further comprising isolating the ear engaging members from the eye protector connectors in both the first and second modes such that (a) the ear engaging members do not disturb operation of the eye protector connectors when in use and (b) the eye protector connectors do not disturb operation of the ear engaging members when in use.

13. The method of claim 11 wherein providing the cord comprises providing two distinct strands and positioning the strands near each other with the dual mode adjustment member.

14. The method of claim 11 further comprising surrounding a portion of the length of the cord between the ear and eye ends with the dual mode adjustment member and frictionally engaging the cord to adjustably shorten or lengthen the length of the cord between the adjustment member and the eye end of the cord.

15. The method of claim 11 wherein further comprising joining at least one of the left ear end, the right ear end, the left eye end, and the right eye end to its respective ear engaging member or eye protector connector with a break-away connection.

16. A method for locating a pair of ear engaging members with an eye protector in proximity to a user's head, comprising:
providing a cord comprising (i) a length with an ear end and an opposite eye end and (ii) a dual mode adjustment member located along the length of the cord between the ear and eye ends, wherein the ear end of the cord comprises a left ear end and a right ear end and the eye end of the cord comprises a left eye end and a right eye end;
joining an ear engaging member to each left and right ear end;
joining an eye protector connector to each left and right eye end;
joining the eye protector connectors to the eye protector; and,
positioning the dual mode adjustment member along the length of the cord to (i) a first mode that adjustably shortens the length of the cord between the adjustment member and the eye end of the cord to thereby provide a force to tension the eye protector connectors toward each other and thereby secure the eye protector to the user's head, and (ii) a second mode that adjustably lengthens the length of the cord between the adjustment member and the eye end of the cord to thereby reduce the tension between the eye protector connectors and enable them to be moved further away from each other and thereby unsecure the eye protector from the user's head.

17. The method of claim 16 wherein positioning comprises isolating the ear engaging members from the eye connector members in both the first and second modes such that (a) the ear engaging members can hang from the user while not in use without disturbing operation of the eye protector connectors in use and (b) the eye protector members can hang from the user while not in use without disturbing operation of the ear engaging members when in use.

18. The method of claim 16 wherein providing the cord comprises providing two distinct strands and positioning the strands near each other with the dual mode adjustment member.

19. The method of claim 16 further comprising surrounding a portion of the length of the cord between the ear and eye ends with the dual mode adjustment member and frictionally engaging the cord to adjustably shorten or lengthen the length of the cord between the adjustment member and the eye end of the cord.

20. The method of claim 16 wherein further comprising joining at least one of the left ear end, the right ear end, the left eye end, and the right eye end to its respective ear engaging member or eye protector connector with a break-away connection.

* * * * *